(12) United States Patent
Murayama et al.

(10) Patent No.: US 7,632,237 B2
(45) Date of Patent: Dec. 15, 2009

(54) GUIDE WIRE AND METHOD OF MANUFACTURING THE GUIDE WIRE

(75) Inventors: Hiraku Murayama, Fujinomiya (JP); Katsuro Mishima, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 10/802,869

(22) Filed: Mar. 18, 2004

(65) Prior Publication Data

US 2004/0260206 A1 Dec. 23, 2004

(30) Foreign Application Priority Data

Mar. 18, 2003 (JP) .............................. 2003-074313

(51) Int. Cl.
*A61M 25/00* (2006.01)
*A61M 5/178* (2006.01)
(52) U.S. Cl. .................... 600/585; 600/433; 600/434; 604/164.03
(58) Field of Classification Search .............. 600/585, 600/433, 434; 604/164.3, 164.03
See application file for complete search history.

(56) References Cited

U.S. PATENT DOCUMENTS

| 5,171,383 | A | | 12/1992 | Sagae et al. |
| 5,533,985 | A | * | 7/1996 | Wang ........................... 604/264 |
| 5,554,139 | A | * | 9/1996 | Okajima ....................... 604/526 |
| 5,622,665 | A | * | 4/1997 | Wang ........................... 264/150 |
| 6,001,068 | A | * | 12/1999 | Uchino et al. ................ 600/585 |
| 6,328,822 | B1 | * | 12/2001 | Ishida et al. .................. 148/436 |
| 2003/0069520 | A1 | * | 4/2003 | Skujins et al. ............... 600/585 |
| 2003/0181828 | A1 | * | 9/2003 | Fujimoto et al. ............. 600/585 |
| 2004/0167437 | A1 | * | 8/2004 | Sharrow et al. .............. 600/585 |

FOREIGN PATENT DOCUMENTS

| JP | 05-278158 | 10/1993 |
| JP | 11-057014 | 3/1999 |
| JP | 11-315973 | 11/1999 |
| JP | 2001-192707 | 7/2001 |

OTHER PUBLICATIONS

Official Action for corresponding Japanese Application No. 2003-74313 dated Dec. 2, 2008.
Official Action for corresponding Japanese Application No. 2003-74313 dated Jun. 16, 2009.

* cited by examiner

*Primary Examiner*—Max Hindenburg
*Assistant Examiner*—Jeffrey G Hoekstra
(74) *Attorney, Agent, or Firm*—Buchanan Ingersoll & Rooney PC

(57) ABSTRACT

A guide wire includes a distal end side portion formed of a first metallic material, a proximal end side portion formed of a second metallic material higher in rigidity than the first metallic material, and an intermediate portion provided between the distal end side portion and the proximal end side portion and formed of a mixture of the first metallic material and the second metallic material. The intermediate portion includes a gradient physical property portion in which the content of the second metallic material increases from the distal end side toward the proximal end side.

19 Claims, 7 Drawing Sheets

GUIDE WIRE AND METHOD OF MANUFACTURING THE GUIDE WIRE

BACKGROUND OF THE INVENTION

The present invention relates to a guide wire, particularly to a guide wire for use in introducing a catheter into a body lumen such as a blood vessel, and to a method of manufacturing the same.

Guide wires are used to guide a catheter in treatment of cites at which open surgeries are difficult or which require low invasion to the body, for example, PTCA (Percutaneous Transluminal Coronary Angioplasty), or in diagnosis such as cardioangiography, and for the like purposes.

A guide wire used in the PTCA procedure is inserted, with its distal end projecting from the distal end of a balloon catheter, into the vicinity of a target angiostenosis portion together with the balloon catheter, and is thus used to guide the distal end portion of the balloon catheter to the vicinity of the target angiostenosis portion.

Particularly, a guide wire used to insert a balloon catheter into a blood vessel is required to go forward in a complicatedly meandering blood vessel, and is therefore required to have sufficient flexibility and restoring performance against bending, pushability and torque transmission performance (these are altogether called operationality) for securely transmitting an operational force from the proximal end portion to the distal end side, kink resistance, and the like. As this kind of guide wire used for a catheter, there have been proposed a guide wire in which a coil having flexibility against bending is disposed around a small-diameter core member for providing the distal end portion with appropriate flexibility, and a guide wire comprising a core member formed of a superelastic material such as a Ni—Ti alloy for attaining flexibility and restoring performance.

In the conventional guide wires, the core member is substantially made of a single material. Therefore, the flexibility of the distal end portion of the guide wire is lost where a material having a comparatively high elastic modulus is used for forming the core member in order to enhance the operationality of the guide wire. On the other hand, if a material having a comparatively low elastic modulus is used for the core member in order to obtain flexibility at the distal end portion of the guide wire, the operationality on the proximal end side of the guide wire is lost. Thus, it has been regarded as difficult to satisfy both the requirements of flexibility and operationality by using a core member made of a single material.

For solving the above problem, there has been proposed a guide wire in which a Ni—Ti alloy wire is used as a core member, and the distal end side and the proximal end side of the alloy wire are heat-treated under different conditions in order to enhance the flexibility of the distal end portion of the alloy wire and to enhance the rigidity on the proximal end side of the alloy wire (U.S. Pat. No. 5,171,383). However, such a control of flexibility by heat treatments has a limitation; for example, even if a sufficient flexibility is obtained at the distal end portion of the alloy wire, a satisfactory rigidity may not necessarily be obtained on the proximal end side of the alloy wire.

Also, there has been proposed a guide wire which is comprised of a flexible wire disposed on the distal end side, a high-rigidity wire disposed on the proximal end side, and a tubular joint member connecting the first wire and the second wire and being provided with a groove and a slit, wherein the rigidity of the joint member increases gradually from the distal end side toward the proximal end side (U.S. Pat. No. 6,001,068). This guide wire shows a sufficient effect. However, there is still a demand for a guide wire in which the variation in physical property is more gradual, the torque transmitting force and pushing force can be transmitted from the proximal end portion to the distal end side more securely, and the distal end portion is more flexible.

The present invention has been made in consideration of the above-mentioned problems in the prior art.

It is an object of the present invention to provide a guide wire having a sufficiently flexible distal end portion and further enhanced in torque transmission performance and pushability, and a method of manufacturing the same.

SUMMARY OF THE INVENTION

In accordance with the present invention, the objects described above are achieved by a guide wire that comprises a distal end side portion formed of a first metallic material, a proximal end side portion formed of a second metallic material higher in rigidity than said first metallic material, and an intermediate portion provided between said distal end side portion and said proximal end side portion and formed of a mixture of said first metallic material and said second metallic material, wherein said intermediate portion comprises a gradient physical property portion in which the content of said first metallic material decreases and the content of said second metallic material increases, from the distal end side toward the proximal end side.

In accordance with the present invention, the objects described above are achieved by a guide wire that comprises a distal end side portion formed of a first metallic material, a proximal end side portion formed of a second metallic material higher in rigidity than said first metallic material, and an intermediate portion provided between said distal end side portion and said proximal end side portion and having a portion of formed of a mixture containing said first metallic material, said intermediate portion comprises a gradient physical property portion in which the content of said first metallic material decreases from the distal end side toward the proximal end side, a distal end portion of said intermediate portion is formed of said first metallic material, and said distal end portion of said intermediate portion is joined to said distal end side portion by welding.

In accordance with the present invention, the objects described above are achieved by a guide wire that comprises a distal end side portion formed of a first metallic material, a proximal end side portion formed of a second metallic material higher in rigidity than said first metallic material, and an intermediate portion provided between said distal end side portion and said proximal end side portion and having a portion of formed of a mixture containing said first metallic material and said second metallic material, and said portion of said intermediate portion is that the content of said first metallic material decreases from the distal end side toward the proximal end side and the content of said second metallic material increases from the distal end side toward the proximal end side, a distal end portion of said intermediate portion is formed of said first metallic material, and a proximal end portion of said intermediate portion is formed of said second metallic material, and said distal end portion of said intermediate portion is joined to said distal end side portion by welding and said proximal end portion of said intermediate portion is joined to said proximal end side portion by one of welding, soldering or brazing.

In accordance with the present invention, the objects described above are achieved by a guide wire that comprises a distal end side portion formed of a first metallic material, a proximal end side portion formed of a second metallic material higher in rigidity than said first metallic material, and an intermediate portion provided between said distal end side portion and said proximal end side portion and containing said first metallic material and said second metallic material, said intermediate portion comprises a gradient physical property portion in which the content of said first metallic material decreases from the distal end side toward the proximal end side, and in which the content of said second metallic material increases from the distal end side toward the proximal end side, a distal end portion of said intermediate portion is formed only of said first metallic material, and a proximal end portion of said intermediate portion is formed only of said second metallic material, and said distal end portion of said intermediate portion is joined to said distal end side portion by welding and said proximal end portion of said intermediate portion is joined to said proximal end side portion by one of welding soldering or brazing.

In accordance with the present invention, the objects described above are achieved by a method of manufacturing a guide wire that comprises a distal end side portion formed of a first metallic material, a proximal end side portion formed of a second metallic material higher in rigidity than said first metallic material, and an intermediate portion provided between said distal end side portion and said proximal end side portion and formed of a mixture of said first metallic material and said second metallic material, said method comprises the steps of: preparing a distal end side portion forming wire material made of said first metallic material, and a proximal end side portion forming wire material made of said second metallic material; charging a mold with a powder of said first metallic material and a powder of said second metallic material so that the content of said first metallic material powder increases and the content of said second metallic material powder decreases, from one side toward the other side; sintering the metallic powder charge to produce an intermediate portion forming member comprising a gradient physical property portion; and joining said proximal end side portion forming wire material to one side of said intermediate portion forming member and joining said distal end side portion forming wire material to the other side of said intermediate portion forming member.

In accordance with the present invention, the objects described above are achieved by a method of manufacturing a guide wire that comprises a distal end side portion formed of a first metallic material, a proximal end side portion formed of a second metallic material higher in rigidity than said first metallic material, and an intermediate portion provided between said distal end side portion and said proximal end side portion and formed of a mixture of said first metallic material and said second metallic material, said method comprises a step of continuously extruding into a filamentous shape a kneaded forming material containing a metallic powder for forming said guide wire, and a step of sintering the filamentous body thus extruded, said kneaded forming material extruding step comprising: a distal end side portion forming material extruding stage for extruding a material containing said first metallic powder into a filamentous shape; a proximal end side portion forming material extruding stage for extruding a material containing said second metallic powder into a filamentous shape; and an intermediate portion forming material extruding stage which is provided between, and continuous with, said distal end side portion forming material extruding stage and said proximal end side portion forming material extruding stage and which is for extruding a material containing said first metallic powder and said second metallic powder, wherein during said intermediate portion forming material extruding stage, the extrusion is so conducted that the content of said first metallic powder in the intermediate portion forming material decreases and the content of said second metallic material in the intermediate portion forming material increases, as said proximal end side portion forming material extruding stage is approached.

DETAILED DESCRIPTION OF THE PREFERRED EMBODIMENTS

Guide wires according to embodiments of the present invention will be described below referring to the accompanying drawings.

Figure 1:
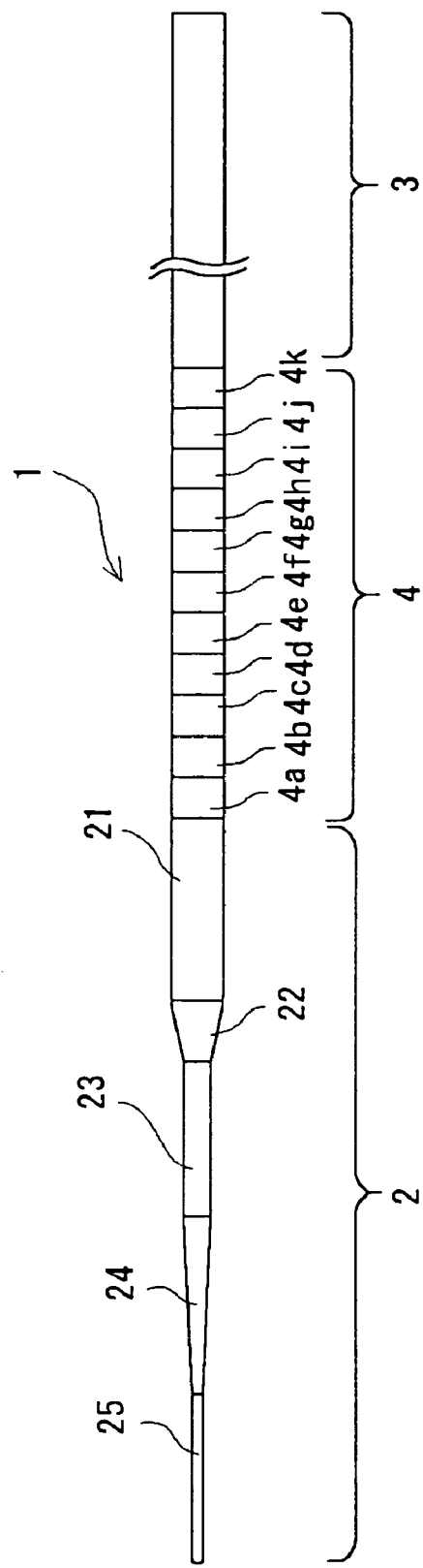
FIG. 1 is a front view of a guide wire according to one embodiment of the present invention.

FIG. 1 is a front view of a guide wire according to one embodiment of the present invention.

A guide wire 1 according to the present invention includes a distal end side portion 2 formed of a first metallic material, a proximal end side portion 3 formed of a second metallic material higher in rigidity than the first metallic material, and an intermediate portion 4 provided between the distal end side portion 2 and the proximal end side portion 3 and formed of a mixture of the first metallic material and the second metallic material. The intermediate portion includes a gradient physical property portion 4 in which the content of the first metallic material decreases while the content of the second metallic material increases from the distal end side toward the proximal end side.

The guide wire 1 is a medical guide wire used in the state of being inserted in the lumen of a catheter (not shown). As shown in FIG. 1, the guide wire 1 includes the distal end side portion 2, the proximal end side portion 3, and the intermediate portion including the gradient physical property portion 4 disposed between the distal end side portion 2 and the proximal end side portion 3. The distal end side portion 2 is more flexible than the proximal end side portion 3. The overall length of the guide wire is not particularly limited, it being preferably about 200 to 5000 mm. In addition, the outside diameter of the guide wire, exclusive of a small-diameter portion on the distal end side thereof, is preferably about 0.2 to 1.2 mm.

In the guide wire 1 in this embodiment, as shown in FIG. 1, the distal end side portion 2 includes a cylindrical portion 21 formed on the proximal end side thereof, and the small-diameter portion formed on the distal side of the cylindrical portion 21. The small-diameter portion is comprised of a first tapered portion 22 reduced in diameter toward the distal end thereof, a cylindrical portion 23 formed on the distal side of the first tapered portion 22, a second tapered portion 24 formed on the distal side of the cylindrical portion 23 and gradually reduced in diameter toward the distal end thereof, and a substantially cylindrical portion 25 formed on the distal side of the second tapered portion 24.

With such a configuration, the rigidity of the distal end side portion 2 gradually decreases toward the distal end, and, therefore, the guide wire 1 is enhanced in compliance with a blood vessel and in safety, and is enhanced in resistance to kinking or the like. Two tapered portions reduced in diameter toward the distal end are provided in this embodiment of the present invention. Three or more tapered portions may be provided, or only one tapered portion may be provided. Further, the distal end side portion 2 may be provided with no tapered portion. In addition, a distal end portion of the cylindrical portion (small-diameter portion) 25 is preferably produced to be round. Besides, the diameters of the tapered portion 22 and the tapered portion 24 of the distal end side portion 2 are each decreased toward the distal end at a constant rate. Therefore, the variation in the rigidity (flexural rigidity, and torsional rigidity) is gradual. The length of the distal end side portion 2 is preferably about 20 to 1000 mm, particularly about 50 to 200 mm. In addition, the diameter of the proximal end portion of the distal end side portion 2 is preferably substantially equal to the diameter of the intermediate portion (gradient physical property portion) 4 and the proximal end side portion 3. The distal end side portion 2 may have a substantially equal diameter over the whole length thereof, or may be reduced in diameter in a tapered form toward the distal end side over the whole length thereof.

The distal end side portion 2 is made of a first metallic material. As the first metallic material, a material lower in rigidity than a second metallic material which will be described later is used. The first metallic material is preferably a metal which shows pseudo-elasticity such as a super-elastic metal, for example. Stainless steels (for example, SUS304, SUS303, SUS316, SUS316L, SUS316J1, SU316J1L, SUS405, SUS430, SUS434, SUS444, SUS429, SUS430F, SUS302,etc.) may also be used as the first metallic material.

The first metallic material is preferably a Ni—Ti based alloy. More preferably, the first metallic material is a Ni—Ti alloy which shows pseudo-elasticity. With the distal end side portion of the guide wire formed of such an alloy, the distal end side portion becomes a flexible portion. When a metallic material capable of showing pseudo-elasticity (also called a pseudo-elastic alloy) is used as the first metallic material, the distal end side portion 2 has sufficient flexibility and restoring performance, so that it is possible to obtain high compliant performance in relation to complicatedly curved or meandering blood vessels and high operationality. In addition, the high restoring performance of the pseudo-elastic alloy ensures that the distal end side portion 2 will not show a substantially permanent bend even when subjected to repeated curving or bending, and the operationality of the guide wire 1 can be prevented from being lowered due to a substantially permanent bend.

The pseudo-elastic alloys may include those showing any tensile stress-strain curves, and may include not only those whose transformation points such as As, Af, Ms, and Mf can be measured conspicuously but also those whose transformation points cannot be measured conspicuously. Thus, the pseudo-elastic alloys include all of those which are largely deformed (strained) under a stress and which substantially restore the original shape thereof upon removal of the stress.

Examples of the metallic material capable of showing pseudo-elasticity include Ni—Ti based alloys, Cu—Zn alloys, Cu—Zn—X alloys (where X is at least one of Be, Si, Sn, Al, and Ga), and Ni—Al alloys. Specifically, preferable examples include Ni—Ti based alloys such as Ni—Ti alloys containing 49 to 52 at % of Ni, Cu—Zn alloys containing 38.5 to 41.5 wt % of Zn, Cu—Zn—X alloys (where X is at least one of Be, Si, Sn, Al, and Ga) containing 1 to 10 wt % of X, and Ni—Al alloys containing 36 to 38 at % of Al. As the first metallic material, particularly preferred are the Ni—Ti based alloys.

The proximal end side portion 3 is a filamentous portion having a substantially constant diameter. The proximal end side portion 3 is made of a second metallic material which is higher in rigidity than the first metallic material. The proximal end side portion 3 is preferably composed of a material which is higher in rigidity (at least one of modulus of longitudinal elasticity, modulus of transverse elasticity, bulk modulus, yield point, maximum stress) than the material of the distal end side portion 2. With the proximal end side portion 3 made of the second metallic material having a high rigidity, the guide wire 1 will show excellent operationality (pushability and torque transmission performance).

As the second metallic material, there can be used various metallic materials such as stainless steels (for example, SUS304, SUS303, SUS316, SUS316L, SUS316J1, SUS316J1L, SUS405, SUS430, SUS434, SUS444, SUS429, SUS430F, SUS302,etc.), piano wire, high-carbon steels, and cobalt-based alloys. The second metallic material is preferably the stainless steels or cobalt-based alloys.

The length of the proximal end side portion 3 is preferably about 20 to 4800 mm, particularly about 50 to 1500 mm. In addition, the diameter of the proximal end side portion 3 is preferably substantially equal to the diameter of the distal end side portion 2 exclusive of the small-diameter portion on the distal end side thereof and the diameter of the gradient physical property portion 4, and is preferably about 0.2 to 1.6 mm, particularly about 0.3 to 1.0 mm.

The intermediate portion 4 is a cylindrical filamentous portion. The intermediate portion 4 is provided between the distal end side portion 2 and the proximal end side portion 3, and includes a gradient physical property portion made by use of a mixture of the first metallic material and the second metallic material. In the embodiment shown in FIG. 1, the gradient physical property portion 4 contains the second metallic material in a content increasing stepwise from the distal end side toward the proximal end side in the axial direction thereof. The gradient physical property portion 4 may be provided sequentially with gradient physical property portion forming layers 4b,4c,4d,4e,4f,4g, 4h,4i,and 4j in which the content of the second metallic material increases stepwise from the distal end side toward the proximal end side. In addition, the content of the second metallic material preferably increases at a constant rate from the distal end side toward the proximal end side. This ensures that the rigidity gradually increases from the distal end side toward the proximal end side of the guide wire 1, so that torque transmission performance and pushability are further enhanced.

The gradient physical property portion 4 may be provided sequentially with gradient physical property portion forming layers 4b, 4c,4d,4e,4f,4g,4h,4i,and 4j in which the content of the first metallic material decreases stepwise from the distal end side toward the proximal end side. The content of the first metallic material preferably decreases at a constant rate from the distal end side toward the proximal end side.

Besides, in this embodiment of the present invention, the weight ratios of the first metallic material to the second metallic material in the gradient physical property portion forming layers 4b to 4j are, for example, 90:10, 80:20, 70:30, 60:40, 50:50, 40:60, 30:70, 20:80, and 10:90. While the gradient physical property portion forming layers in the present invention are composed of the nine kinds of forming layers in which the content of the second metallic material increases at a constant rate toward the proximal end side, this is not limitative. For example, the gradient physical property portion forming layers may be composed of not less than ten layers, or not more than eight layers, in which the content of the second metallic material increases at a constant rate. Besides, the content of the second metallic material may increase stepwise at a constant rate, or at a rate which increases or decreases toward the proximal end side, over the whole of the gradient physical property portion forming layers.

The intermediate portion 4 may contain the first metallic material, the second metallic material and other materials which are higher rigidity than the first metallic material. The intermediate portion 4 may have a portion formed of a mixture containing the first metallic material and at least one material, which is preferably higher rigidity than the first metallic material.

In addition, a distal end portion of the intermediate portion 4 is preferably made of the first metallic material. In this embodiment of the present invention, a layer 4a made of the first metallic material and not containing the second metallic material is formed on the distal end side of the forming layer 4b. This configuration makes it easy to join the distal end of the intermediate portion 4 and the distal end side portion 2 to each other.

Besides, a proximal end portion of the intermediate portion 4 is preferably made of the second metallic material. In this embodiment of the present invention, a layer 4k made of the second metallic material and not containing the first metallic material is formed on the proximal end side of the forming layer 4j. This configuration makes it easy to join the proximal end of the intermediate portion 4 and the proximal end side portion 3 to each other.

With the gradient physical property portion 4 provided in this manner, the rigidity decreases smoothly from a central portion toward the distal end side, so that the guide wire 1 is excellent in operationality (pushability and torque transmission performance).

Then, the guide wire 1 is produced integrally by joining the proximal end of the distal end side portion 2 and the distal end of the intermediate portion 4 to each other and joining the distal end of the proximal end side portion 3 and the proximal end of the intermediate portion 4 to each other. Examples of the joining include spot welding by use of a laser, and butt resistance welding such as butt seam welding, among which resistance welding is preferred.

Joining the distal end side portion 3 and the proximal end of the intermediate portion 4 to each other particularly is not limited by welding. For example the joining may include brazing, soldering, clamping or adhering with sleeve.

The guide wire 1 is not limited to those formed by the above-mentioned joining process. The guide wire 1 may be an integral body which includes the distal end side portion 2, the intermediate portion 4 including the gradient physical property portion and the proximal end side portion 3, and which does not include any joint portion. This configuration ensures that the rigidity decreases smoothly from the intermediate portion toward the distal end side, so that the guide wire 1 is excellent in operationality (pushability and torque transmission performance).

Next, a guide wire according to another embodiment of the present invention will be described referring to the accompanying drawings.

Figure 2:
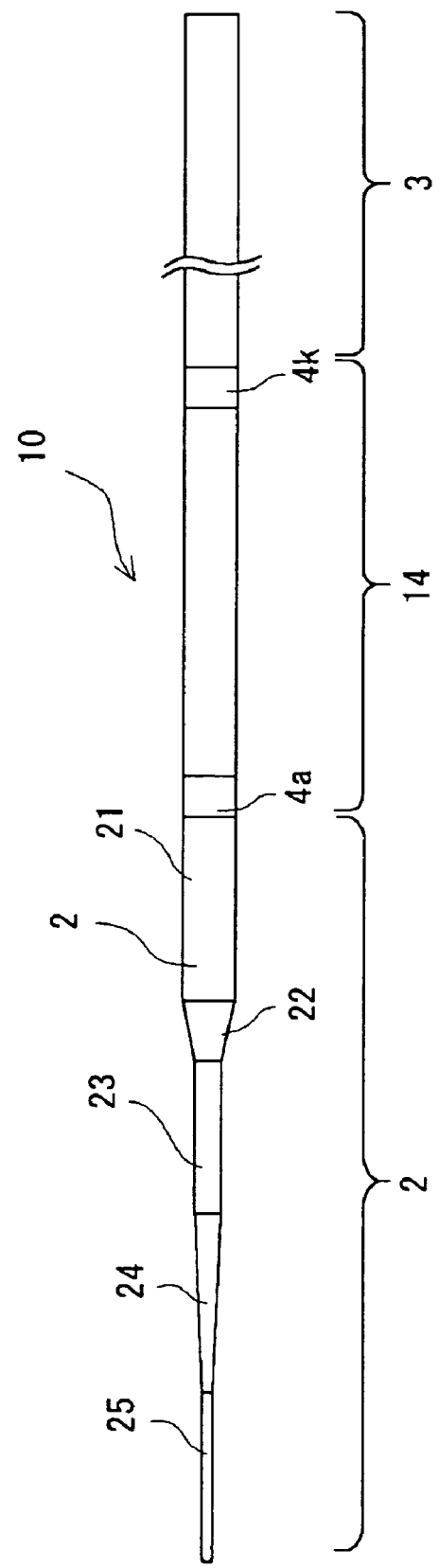
FIG. 2 is a front view of a guide wire according to another embodiment of the present invention.

FIG. 2 is a front view of the guide wire according to the another embodiment of the present invention.

This guide wire 10 differs from the above-described guide wire 1 only in the configuration of an intermediate portion 14 including a gradient physical property portion. The following description will be centered on the difference.

As shown in FIG. 2, the guide wire 10 is comprised of a distal end side portion 2, a proximal end side portion 3, and the intermediate portion 14 including the gradient physical property portion. The distal end side portion 2 and the proximal end side portion 3 are the same as those described above, and, therefore, the above descriptions thereof are referred to.

The intermediate portion 14 is provided between the distal end side portion 2 and the proximal end side portion 3 and is made by use of a mixture of the first metallic material and the second metallic material, with the content of the second metallic material increasing and the content of the first metallic material decreasing from the distal end side toward the proximal end side. Particularly, in this embodiment, the content of the second metallic material in the gradient physical property portion increases continuously, or gradually, from the distal end side toward the proximal end side. In this embodiment, the content of the second metallic material increases continuously at a constant rate. In addition, the content of the second metallic material may increase continuously at a constant rate, or at a rate which increases or decreases toward the proximal end side, over the whole of the intermediate portion 14.

Besides, a distal end portion of the intermediate portion 14 is preferably made of the first metallic material, as described above. Specifically, in this embodiment, a layer 4a made of the first metallic material and not containing the second metallic material is formed at the distal end portion of the intermediate portion 14. This configuration makes it easy to join the distal end of the intermediate portion 14 and the distal end side portion 2 to each other. In addition, a proximal end portion of the intermediate portion 14 is preferably made of the second metallic material. Specifically, in this embodiment, a layer 4k made of the second metallic material and not containing the first metallic material is formed at the proximal end of the gradient physical property portion 14. This configuration makes it easy to join the proximal end of the intermediate portion 14 and the proximal end side portion 3 to each other.

Then, the guide wire 10 is produced integrally by joining the proximal end of the distal end side portion 2 and the distal end of the intermediate portion 14 to each other and joining the distal end of the proximal end side portion 3 and the proximal end of the intermediate portion 14 to each other. The joining is preferably carried out by the above-mentioned method.

In addition, the guide wire 10 is not limited to those formed by the above-mentioned joining. For example, the guide wire 10 may be an integral body which includes the distal end side portion 2, the intermediate portion 14 having the gradient physical property portion, and the proximal end side portion 3 and which does not include any joint portion. Where the guide wire is such an integral body not comprising any joint portion, the guide wire as a whole is free of a point of abrupt change in physical properties and, therefore, shows favorable operationality.

Besides, the guide wire may have an outer surface coated with a resin. The resin is desirably a thermoplastic resin. Examples of the usable thermoplastic resin include olefin-based resins or polyolefin-based elastomers such as polyethylene, polypropylene, polybutene, ethylene-vinyl acetate copolymer, etc.; fluororesins or soft fluororesins; polyesters or polyester-based elastomers such as polyethylene terephthalate, polybutylene terephthalate, etc.; methacrylic resin; polyphenylene oxide; modified polyphenylene ether; polyurethane or polyurethane-based elastomers; polyamides or polyamide-based elastomers; polycarbonate; polyacetal; styrene-based resins or styrene-based elastomers such as polystylene, stylene-butadiene copolymer, etc.; thermoplastic polyimides; and polyvinyl chloride. In addition, polymer alloys or polymer blends based on these resins may also be used. Furthermore, rubbers such as natural rubber, isoprene rubber, silicone rubbers, etc. may also be used. Among these materials, particularly preferred are the thermoplastic resins. Besides, the resin coating is preferably so flexible as not to hinder the curving of the guide wire, and the outer surface thereof is preferably a smooth surface free of ruggedness.

Furthermore, the outer surface of the resin coating may be coated with an anticoagulant such as heparin, urokinase, etc. or with an antithrombotiic material such as urethane-silicone block copolymer (registered trademark: Avcothane), hydroxyethyl methacrylate-styrene copolymer, etc.

In addition, a low friction material may be fixed to the surface of the resin coating. The fixation of the low friction material may be carried out only at a distal end portion or carried out at the portion exclusive of a proximal end portion. As the low friction material, there may be used hydrophobic materials having a low friction surface independently of wetting thereof, for example, fluororesins and silicone resins, and materials showing lubricity when wetted (lubricating materials). Specific examples of the latter include water-soluble polymeric materials and derivatives thereof. The lubricating material is fixed to the surface of the resin coating by covalent bond or ionic bond. The lubricating materials, on principle, are polymeric materials which are in a chain form free of cross-linkage and have a hydrophilic group such as —OH, —CONH$_2$, —COOH, —NH$_2$, —COO$^-$, —SO$^{3-}$, etc. Furthermore, the lubricating materials are hydrated when wetted (for example, upon contact with blood), thereby developing lubricity.

Specifically, examples of natural water-soluble polymeric materials include starch-based ones such as carboxymethyl starch, dialdehyde starch, etc.; cellulose-based ones such as carboxymethyl cellulose, hydroxyethyl cellulose, etc.; tannin; lignin-based ones; alginic acid; gum arabic; polysaccharides such as heparin, chitin, chitosan, etc.; and proteins such as gelatin, casein, etc. Examples of synthetic water-soluble materials include polyvinyl alcohol; polyalkylene oxide-based one such as polyethylene oxide; polyalkylene glycol-based one such as polyethylene glycol; acrylic acid-based ones such as sodium polyacrylate; maleic anhydride-based ones such as methyl vinyl ether-maleic anhydride copolymer, sodium salt of methyl vinyl ether-maleic anhydride, ammonium salt of methyl vinyl ether-maleic anhydride, and ethyl ester maleate anhydride copolymer; phthalate-based ones such as polyhydroxyethyl phthalate; water-soluble polyesters such as polydimethylol propionate; acrylamide-based ones such as polyacrylamide hydrolyzate, quaternary product of polyacrylamide, etc.; polyvinyl pyrrolidone; polyethyleneimine; polyethylene sulfonate; and water-soluble nylon. Among these materials, preferred are the maleic anhydride-based ones, and particularly preferred is ethyl maleate anhydride copolymer.

Next, a guide wire according to a further embodiment of the present invention will be described referring to the accompanying drawings.

Figure 3:
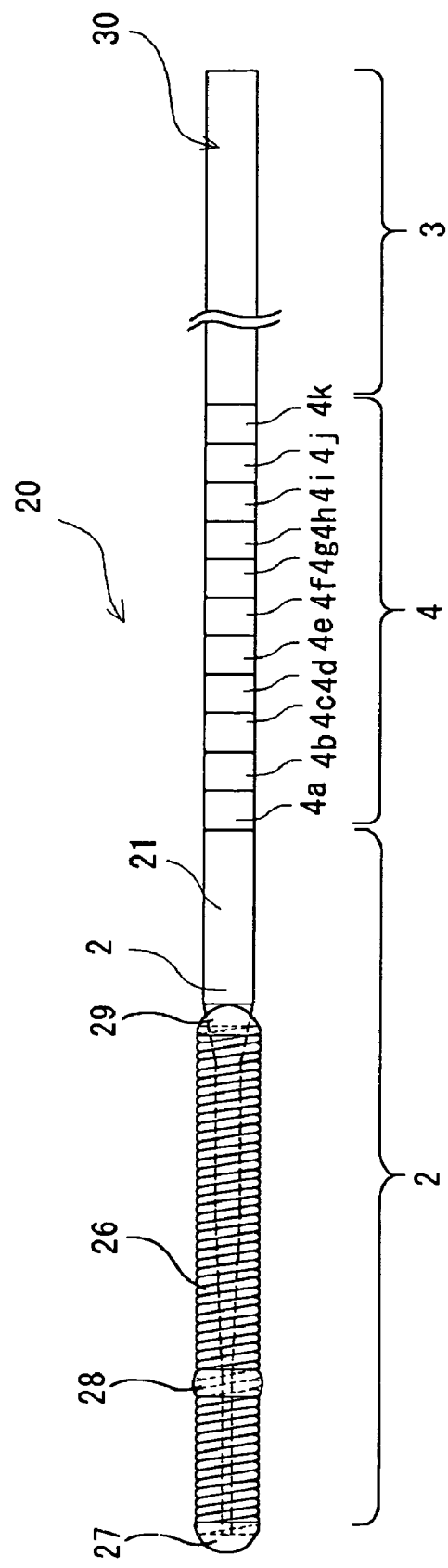
FIG. 3 is a front view of a further embodiment of the present invention.
Figure 4:
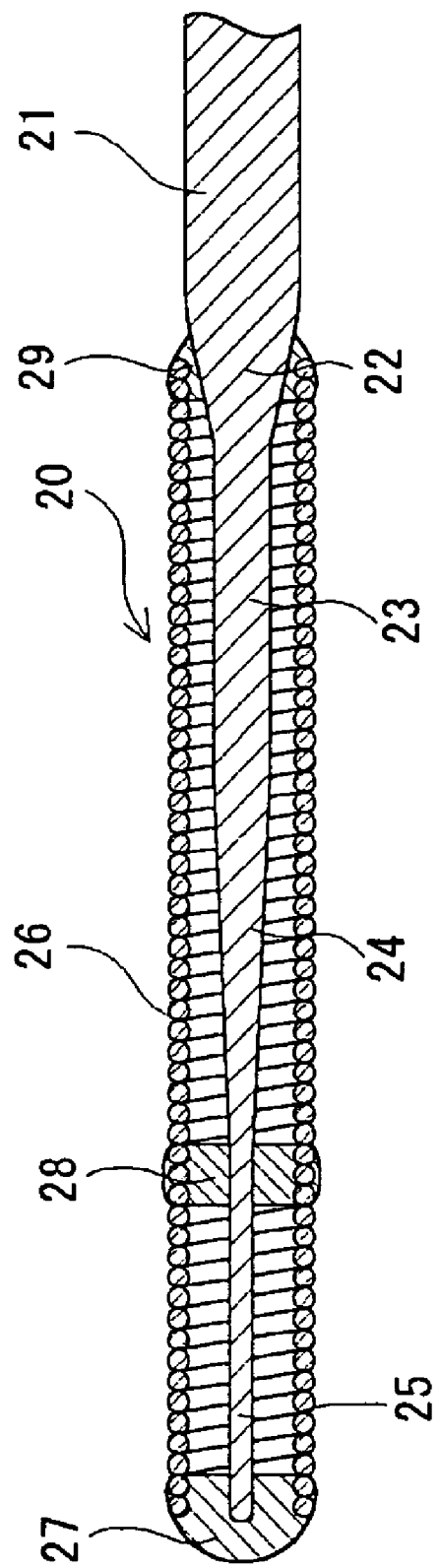
FIG. 4 is an enlarged sectional view of a distal end portion of the guide wire shown in FIG. 3.

FIG. 3 is a front view of the guide wire according to the further embodiment of the present invention, and FIG. 4 is an enlarged sectional view of a distal end portion of the guide wire shown in FIG. 3.

This guide wire 20 according to the present invention differs from the guide wire 1 only in that a coil portion 26 is provided at a distal end portion of the guide wire 20. The following description will be centered on the difference.

As shown in FIG. 3, the guide wire 20 is comprised of a wire portion 30 and the coil portion 26. The wire portion 30 is the same as described above, and description thereof is therefore omitted. In addition, the wire portion 30 in the present invention may be replaced by the above-described guide wire 10. Besides, the guide wire may be one which is formed by the joining as above-described, or may be an integral body which is free of the above-described joint portions.

As shown in FIGS. 3 and 4, the guide wire 20 includes the coil portion 26 so provided as to cover the distal end portion of the guide wire 20.

The coil portion 26 is composed of a member obtained by spirally winding a filamentous material (thin wire), and is so disposed as to cover a small-diameter portion on the distal end side of a distal end side portion 2. The coil portion 26 is preferably so disposed that a distal end portion of the distal end side portion 2 does not make contact with the inside of the coil portion 26. In this embodiment, the small-diameter portion on the distal end side of the distal end side portion 2 is inserted in a central portion of the coil portion 26, and does not make contact with the inside of the coil portion 26.

The coil portion 26 is preferably composed of a metallic material. Examples of the metallic material include stainless steels, superelastic alloys, cobalt-based alloys, noble metals such as gold, platinum, and tungsten, and alloys containing these metals. In addition, the coil portion is preferably made of a high contrast material. Preferred examples of the high contrast material include the above-mentioned noble metals such as gold, platinum, and tungsten. With the coil portion thus made of a high contrast material, it is possible to insert the guide wire into a living body while confirming the position of the distal end portion of the guide wire by radiography, echography or the like. In addition, the coil portion 26 may be formed by use of different materials on the distal end side and on the proximal end side. For example, the distal end side portion of the coil portion 26 may be made of a high contrast material while the proximal end side portion may be made of a material which is not highly radiopaque.

In addition, the coil portion 26 is fixed to the distal end side portion 2 of the guide wire 20 at a distal end portion and a proximal end portion thereof. Besides, the coil portion 26 is preferably fixed to the distal end side portion 2 also at a position between the distal end portion and the proximal end portion thereof. The fixation is preferably carried out by soldering such as brazing, soldering, etc., welding, or adhesion by use of an adhesive. In this embodiment of the present invention, the coil portion 26 is fixed to the distal end side portion 2 at the distal end portion, the proximal end portion, and a rather distal end side position between the distal end portion and the proximal end portion by use of fixing materials 27, 28, and 29 (solder, brazing filler metal). The distal end face of the fixing material 27 at the distal end portion is preferably formed in a rounded shape, in order to prevent it from damaging the inside wall of a blood vessel.

The overall length of the coil portion 26 is not particularly limited, it being preferably 5 to 500 mm, particularly 10 to 200 mm. In addition, the coil portion 26 preferably covers wholly the small-diameter portion on the distal end side of the flexible portion. Besides, the coil wire diameter is preferably 0.01 to 0.1 mm, particularly 0.02 to 0.04 mm.

With the distal end portion of the guide wire 20 covered by the coil portion 26, the area of contact of the distal end side portion 2 with the exterior is reduced, so that sliding resistance can be reduced. As a result, operationality of the guide wire 20 is enhanced.

The outer surface of the guide wire may be coated with a resin. Particularly, the outer surface of the guide wire portion exclusive of the coil portion is preferably coated with a resin. As the resin, the above-mentioned ones can be used.

Next, a method of manufacturing a guide wire according to one embodiment of the present invention will be described.

Figure 5:
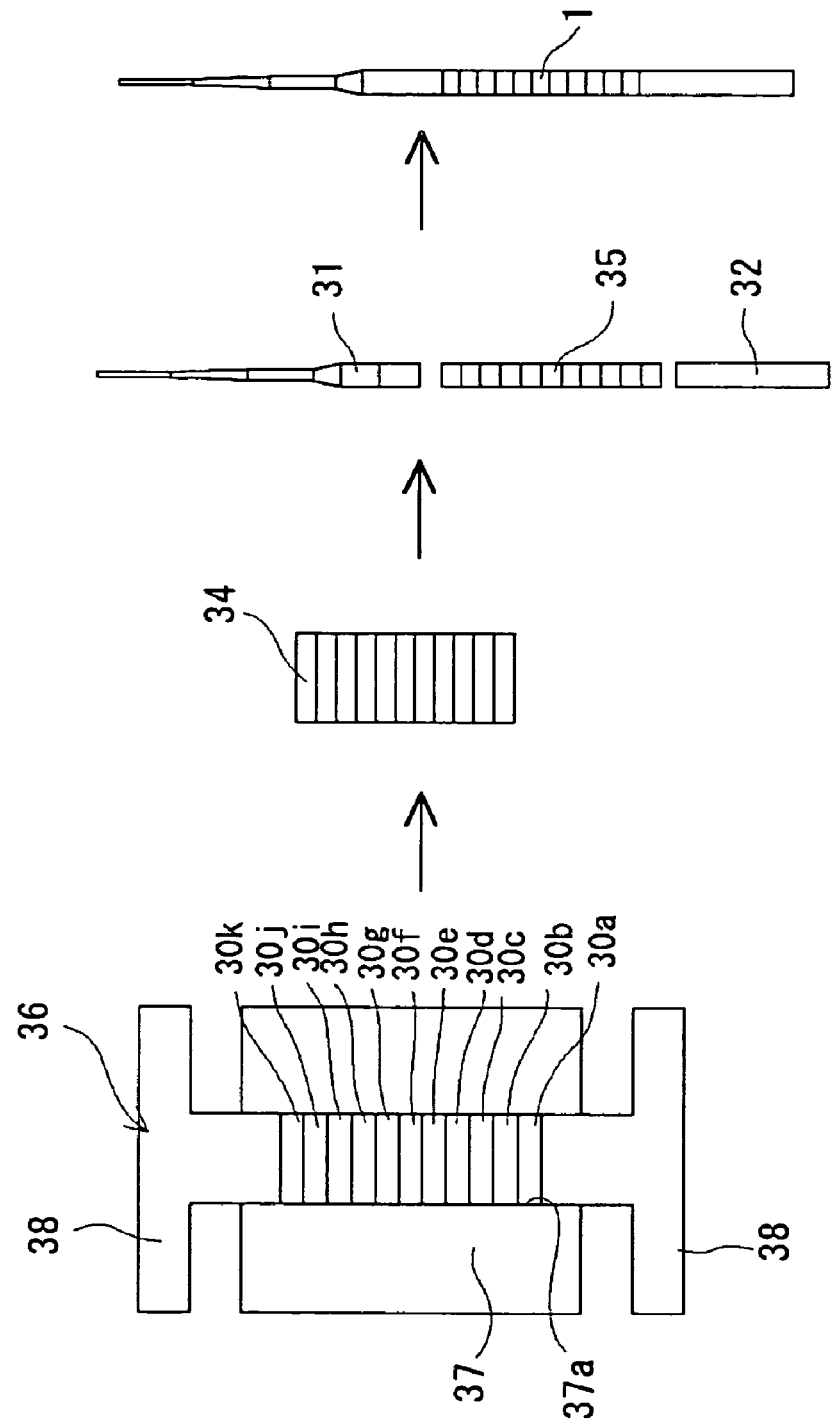
FIG. 5 is an illustration of a method of manufacturing a guide wire according to one embodiment of the present invention.

FIG. 5 is an illustration of the method of manufacturing a guide wire according to one embodiment of the present invention.

The method of manufacturing a guide wire 1 according to the present invention is a method of manufacturing a guide wire which includes a distal end side portion 2 formed of a first metallic material, a proximal end side portion 3 formed of a second metallic material higher in rigidity than the first metallic material, and an intermediate portion 4 provided between the distal end side portion and the proximal end side portion and formed of a mixture of the first metallic material and the second metallic material.

The manufacturing method according to the present invention includes the steps of: preparing a distal end side portion forming wire material 31 made of the first metallic material and a proximal end side portion forming wire material 32 made of the second metallic material; charging a mold with a first metallic material powder and a second metallic material powder so that the content of the first metallic material powder increases while the content of the second metallic material powder decreases from one side toward the other side; sintering the metallic power charge so as to produce an intermediate portion forming member 35 including a gradient physical property portion; and joining the proximal end side portion forming wire material 32 to one side of the intermediate portion forming member 35 and joining the distal end side portion forming wire material 31 to the other side of the intermediate portion forming member 35.

The distal end side portion forming wire material 31 is produced by a known method using the above-mentioned first metallic material. As the first metallic material, the above-mentioned ones may be used. Particularly, the first metallic material is preferably a Ni—Ti based alloy, and more preferably a Ni—Ti based pseudo-elastic alloy. Preferably, the distal end side portion forming wire material 31 is preliminarily processed into the above-mentioned shape.

The proximal end side portion forming wire material 32 is produced by a known method using the above-mentioned second metallic material. As the second metallic material, the above-mentioned ones may be used. Particularly, the second metallic material is preferably a stainless steel, and more preferably SUS304L. The proximal end side portion forming wire material 32 is preferably produced by a known method.

Next, description will be made of the step of charging the mold with the first metallic material powder and the second metallic material powder so that the content of the first metallic material powder increases while the content of the second metallic material powder decreases from one side toward the other side.

The metallic powder charging step comprises, for example, charging the mold with the first metallic material powder and the second metallic material powder so as to form a plurality of layers in which the content of the first metallic material in the charge increases stepwise while the content of the second metallic material in the charge decreases stepwise.

In the metallic powder charging step, a mixture preparing step is conducted to mix the first metallic material and the second metallic material with each other so as to prepare a plurality of mixtures varied in the contents of the first metallic material and the second metallic material. The mixture preparing step is for preparing the plurality of mixtures in which the content of the first metallic material is increased stepwise while the content of the second metallic material is decreased stepwise. First, a powder of the first metallic material and a powder of the second metallic material are prepared. As the first metallic material, one of those mentioned above is used. The first metallic material is preferably a Ni—Ti based alloy, and more preferably a Ni—Ti based pseudo-elastic alloy. In addition, as the first metallic material, the same one as the first metallic material used for forming the distal end side portion forming wire material may be used. As the second metallic material, one of those mentioned above is used. The second metallic material is preferably a stainless steel, and more preferably SUS304L. Besides, as the second metallic material, the same one as the second metallic material used for forming the proximal end side portion forming wire material may be used.

By mixing the powder of the first metallic material and the powder of the second metallic material with each other, nine kinds of metallic powder mixtures are prepared in which the weight ratios of the first metallic material to the second metallic material are respectively 10:90 (a first layer 30b), 20:80 (a second layer 30c), 30:70 (a third layer 30d), 40:60 (a fourth layer 30e), 50:50 (a fifth layer 30f), 60:40 (a sixth layer 30g), 70:30 (a seventh layer 30h), 80:20 (an eighth layer 30i), and 90:10 (a ninth layer 30j). It is preferable to thus prepare the plurality of mixtures such that the contents of the first metallic material and the second metallic material are varied at a fixed rate. In addition, as the metallic powder mixtures prepared, there may be prepared not less than ten kinds of mixtures or not more than eight kinds of mixtures, in which the contents of the first metallic material and the second metallic material are varied at a fixed rate. Besides, as the metallic powder mixtures, there may be prepared a plurality of mixtures such that the contents of the first metallic material and the second material are not varied at a fixed rate.

Next, there is carried out the step of charging the mold with the mixtures so that the content of the first metallic material powder decreases stepwise while the content of the second metallic material powder increases stepwise from one side toward the other side. Specifically, the mixtures prepared as above-mentioned are sequentially laminated in the mold so that the content of the first metallic material increases while the content of the second metallic material decreased from the lower layer toward the upper layer (or from the upper layer toward the lower layer).

To be more specific, as shown in FIG. 5, the nine kinds of mixtures are sequentially laminated in the inside 37a of a sintering chamber (mold) so that the content of the second metallic material decreases from the lower side (the proximal end side in the gradient physical property portion 4) toward the upper side (the distal end side in the gradient physical property portion 4). In other words, the laminate of the mixtures consists of the first layer 30b,the second layer 30c,the third layer 30d,the fourth layer 30e,the fifth layer 30f,the sixth layer 30g,the seventh layer 30h,the eight layer 30i,and the ninth layer 30j laminated in this order, i.e., in the decreasing order of the content of the second metallic material.

In addition, the metallic powder charging step is preferably conducted in such a manner that a second metallic member 30a formed of a second metallic material is placed on one side in the mold, while a first metallic member 30k formed of a first metallic material is placed on the other side in the mold, and the above-mentioned charge is pressed between the metallic members.

Specifically, in the step of charging the mold with the metallic powder mixtures, it is preferable that the second metallic member 30a made of the second metallic material is placed on one side (the lower side in FIG. 5, or the side on which the content of the second metallic material is higher) of the laminate of the mixtures. It is preferable that the first metallic member 30k made of the first metallic material is placed on the other side (the upper side in FIG. 5, or the side on which the content of the first metallic material is higher). The first metallic material and the second metallic material are the same as mentioned above.

Particularly, as the metallic material of the first metallic member, there may be used the same one as the first metallic material used for forming the distal end side portion forming wire material and used in the metallic powder mixtures. As the metallic material of the second metallic member, there may be used the same one as the second metallic material used for forming the proximal end side portion forming wire material and used in the metallic powder mixtures. By use of the two metallic members as above-mentioned, compression of the metallic powder charge is facilitated, and the strength at both end portions of an intermediate portion forming wire material 34 thus formed is enhanced. Furthermore, joining of one end of the intermediate portion forming wire member 34 to the proximal end side portion forming wire material 32 and joining of the other end of the intermediate portion forming wire material 34 to the distal end side portion forming wire material 31 are facilitated.

Next, description will be made of the step of sintering the laminate to produce the intermediate portion forming member having a gradient physical property.

The sintering is preferably carried out by a pressure sintering method such as a hot press sintering method, a discharge plasma sintering method, a resistance heating sintering method, a hot isostatic pressure sintering method (HIP), etc. Particularly, in order to obtain firm binding between powder particles more efficiently, it is preferable to use both the hot press method and the discharge plasma sintering method or to use the discharge plasma sintering method.

The sintering apparatus shown in the figure is a discharge plasma sintering apparatus 36, which includes a sintering chamber 37, and a pressing mechanism 38 for pressing the laminate of the mixtures from both ends of the chamber 37. Incidentally, the sintering apparatus may be a hot press apparatus. The above-mentioned laminate is such that each of the layers has a diameter (inside diameter of cylinder) of preferably 5 to 100 mm, particularly 20 to 50 mm, and a thickness of preferably 1 to 20 mm, particularly 1 to 5 mm, and the total thickness of the nine layers is preferably 10 to 150 mm, particularly 10 to 30 mm.

The mixtures 30b to 30j, the first metallic member 30k and the second metallic member 30a are sintered by the discharge plasma sintering method, to produce the intermediate portion forming member 34. The sintering temperature is preferably 1000 to 1600° C., particularly 1200 to 1500° C., and the pressure exerted is preferably 30 to 50 MPa, particularly 30 to 40 MPa. The sintering time is preferably 10 to 20 min, particularly 15 to 20 min.

Next, a part of the intermediate portion forming member 34 produced by the sintering is cut along the major-axial direction to an elongate cylindrical shape having a length of about 10 to 100 mm and an diameter of about 0.35 to 0.65 mm, followed by polishing, to obtain an intermediate portion forming wire material 35 including a gradient physical property portion with an diameter of about 0.2 to 0.5 mm. The cutting is preferably carried out by use of discharge wire cutting, laser cutting or the like, and the polishing is preferably conducted by use of a cylindrical grinder or the like.

Then, the distal end of the above-mentioned proximal end side portion forming wire material 32 was joined to one end of the intermediate portion forming wire material 35, and the proximal end of the distal end side portion forming wire material 31 was joined to the other end of the intermediate portion forming wire material 35, to produce the guide wire 1 which comprises the distal end side portion 2, the proximal end side portion 3, and the intermediate portion 4 comprising the gradient physical property portion. Examples of the joining method include spot welding by laser, and butt resistance welding such as butt seam welding, etc. Among these methods, particularly preferred is the resistance welding.

By the manufacturing method as above-described, it is possible to easily manufacture a guide wire having a sufficiently flexible distal end portion and further enhanced in operationality from the side of a proximal end portion.

Next, a method of manufacturing a guide wire 10 according to another embodiment of the present invention will be described.

Figure 6:
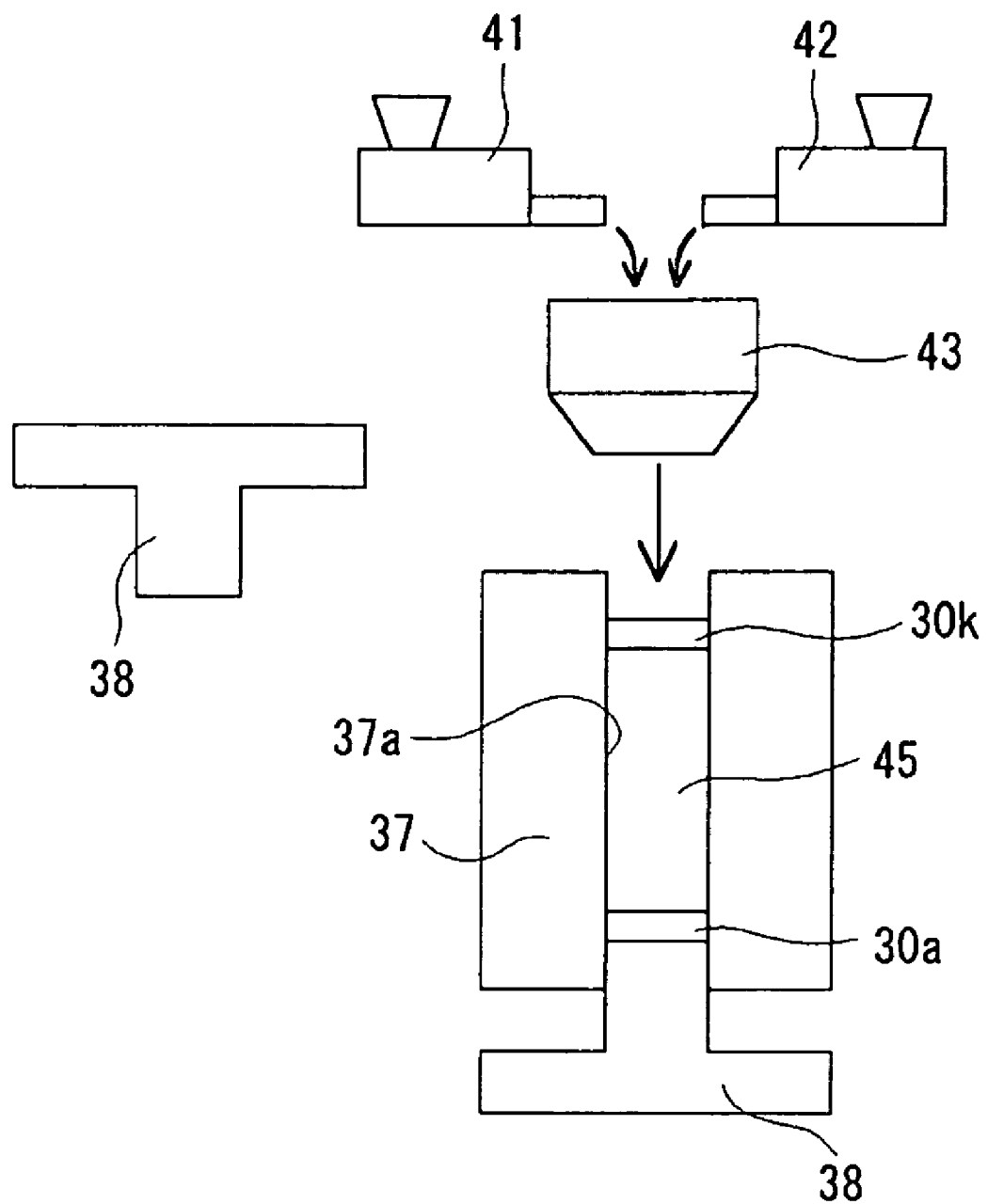
FIG. 6 is an illustration of a method of manufacturing a guide wire according to another embodiment of the present invention.

FIG. 6 is an illustration of the method of manufacturing the guide wire 10 according to the another embodiment of the present invention. The method of manufacturing the guide wire 10 according to the another embodiment of the present invention differs from the above-described method of manufacturing the guide wire 1 only as to the metallic powder charging step. The other points in this method of manufacturing the guide wire 10 may be referred to the above-described method of manufacturing the guide wire 1. The following description will be made of the difference only.

In the method of manufacturing the guide wire according to this embodiment, the metallic powder charging step comprises charging a mold with a first metallic material powder and a second metallic material powder so that the content of a first metallic material in the charge increases continuously while the content of a second metallic material in the charge decreases continuously.

The step of preparing a distal end side portion forming wire material, the step of preparing a proximal end side portion forming wire material, the sintering step, and the joining step are the same as those in the above-described manufacturing method, and, therefore, these steps may be referred to the above.

The metallic powder charging step includes a step of mixing the first metallic material and the second metallic material with each other to prepare a mixture in which the content of the first metallic material and the content of the second metallic material are varied continuously. A laminating step includes a step of charging the mold with the mixture so that the content of the first metallic material increases while the content of the second metallic material decreases, from one end side toward the other end side.

In the method of manufacturing the guide wire 10 according to this embodiment, a manufacturing apparatus as shown in FIG. 6 is used. The manufacturing apparatus includes a first metallic material supply device 41 capable of supplying the first metallic material continuously and variably, a second metallic material supply device 42 capable of supplying the second metallic material continuously and variably, and a mixing device 43 for mixing the first and second metallic materials supplied and for supplying the resulting mixture into a sintering chamber 37. Further, also in this apparatus, the sintering chamber 37 and the pressing mechanism 38 mentioned above are used.

Tie metallic powder charging step will be specifically described below.

First, a powder of the first metallic material and a powder of the second metallic material are prepared. As the first metallic material, one of those mentioned above is used. The first metallic material is preferably a Ni—Ti based alloy, particularly a Ni—Ti based pseudo-elastic alloy. As the first metallic material, there is preferably used the same one as the first metallic material used for forming the distal end side portion forming wire material. Similarly, as the second metallic material, one of those mentioned above is used. The second metallic material is preferably a stainless steel, particularly SUS304L. As the second metallic material, there is preferably used the same one as the second metallic material used for forming the proximal end side portion forming wire material.

Second, the first metallic powder and the second metallic powder are fed into the respective supply devices 41 and 42. The supply devices 41 and 42 are each capable of continuously varying the supply quantity based on the lapse of time. Where the metallic power mixture is fed into the inside 37a of the sintering chamber starting from the mixture portion in which the content of the second metallic material is higher, as in the embodiment shown in FIG. 6, the quantity of the second metallic material supplied decreases continuously at a rate of about 100 g to 0 g/min, while the quantity of the first metallic material increases continuously at a rate of about 0 g to 100 g/min. In this embodiment of the present invention, the quantities of the second metallic material and the first metallic material supplied are each varied at a fixed rate. The quantities of the second metallic material and the first metallic material supplied may not necessarily be varied at a fixed rate. For example, in the case of the embodiment shown in FIG. 6, the rate of increase in the supplied quantity of the first metallic material in a fixed time may be lower in the beginning and may be raised with the lapse of time.

The second metallic material and the first metallic material supplied as above-mentioned are fed into the mixing device 43, in which they are mixed uniformly, and the resulting mixture is fed into the sintering chamber 37. The process from the preparation to the mixing and the process from the mixing to the stacking of the mixture into the sintering chamber 37 are preferably conducted continuously. The mixture of the first metallic material and the second metallic material, with the content of the second metallic material decreasing at a fixed rate with the lapse of time, is stacked in the inside 37a of the sintering chamber. The stack 45 of the mixture of the first metallic material and the second metallic material has a diameter (inside diameter of cylinder) of 5 to 100 mm and a thickness of 10 to 150 mm.

In the metallic powder charging step, it is preferable that a second metallic member 30a made of a second metallic material is placed on one end side (the lower side in FIG. 6) of the charge of the mixture, while a first metallic member 30k made of a first metallic material is placed on the other end side (the upper side in FIG. 6) of the charge of the mixture, in the same manner as in the above-described manufacturing method. The first metallic material and the second metallic material are the same as those mentioned above. Particularly, as the first metallic material of the first metallic member, there may be used the same one as the first metallic material used for forming the distal end side portion forming wire material and used in the metallic powder mixture. As the second metallic material of the second metallic member, there is used the same one as the second metallic material used for forming the proximal end side portion forming wire material and used in the metallic powder mixture.

Then, the sintering of the charge 45, the first metallic member 30k and the second metallic member 30a is conducted as above-mentioned.

By the manufacturing method as described above, it is possible to easily manufacture a guide wire having a sufficiently flexible distal end portion and further enhanced in operationality from the side of a proximal end portion.

Next, a method of manufacturing a guide wire according to a further embodiment of the present invention will be described.

Figure 7:
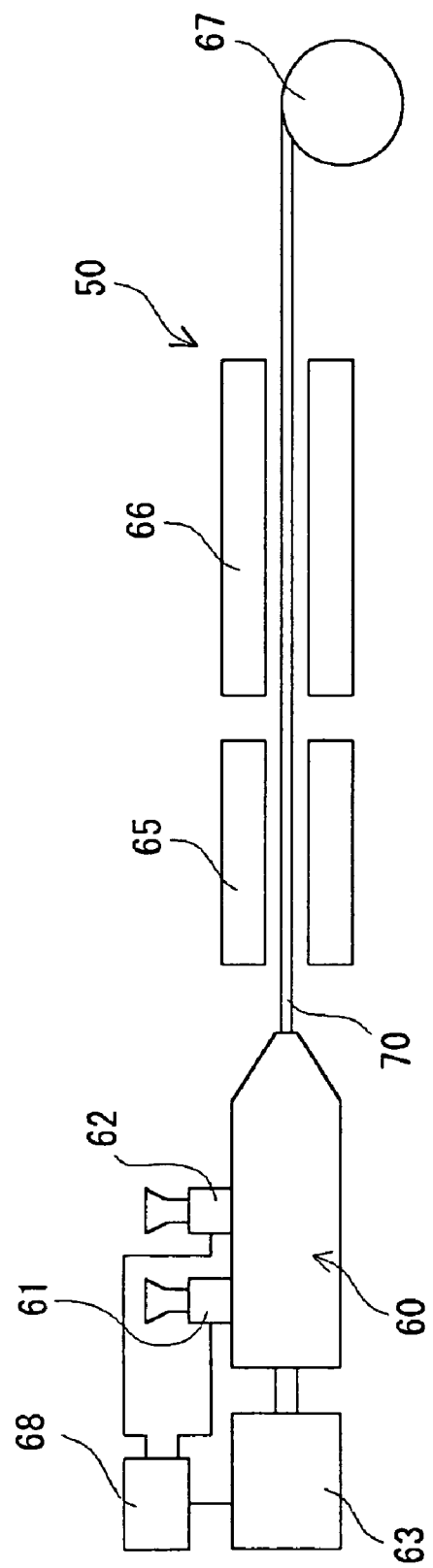
FIG. 7 is an illustration of a method of manufacturing a guide wire according to a further embodiment of the present invention.

FIG. 7 is an illustration of the method of manufacturing a guide wire according to the further embodiment of the present invention.

Similarly to the above-described methods of manufacturing a guide wire, the method of manufacturing a guide wire according to this embodiment is a method of manufacturing a guide wire which includes a distal end side portion formed of a first metallic material, a proximal end side portion formed of a second metallic material higher in rigidity than the first metallic material, and an intermediate portion provided between the distal end side portion and the proximal end side portion and formed of a mixture of the first metallic material and the second metallic material.

This manufacturing method according to the present invention includes a step of continuously extruding into a filamentous shape a kneaded forming material containing a metallic powder for forming a guide wire, and a step of sintering the filamentous body thus extruded. The kneaded forming material extruding step includes a distal end side portion forming material extruding stage for extruding a material containing a first metallic powder into a filamentous shape, a proximal end side portion forming material extruding stage for extruding a material containing a second metallic powder into a filamentous shape, and an intermediate portion forming material extruding stage which is provided between, and continuous with, the distal end side portion forming material extruding stage and the proximal end side portion forming material extruding stage and which is for extruding a material containing the first metallic powder and the second metallic powder. Furthermore, in the intermediate portion forming material extruding stage, the extrusion is so conducted that the content of the first metallic powder in an intermediate portion forming material decreases while the content of the second metallic powder in the intermediate portion forming material increases as the proximal end side portion forming material extruding stage is approached.

The method of manufacturing a guide wire according to the present invention includes the steps of: extruding a forming material while continuously supplying a kneaded forming material containing a binder; removing the binder from the extrudate; sintering the extrudate deprived of the binder; and winding a filamentous body thus sintered.

In the method of manufacturing a guide wire according to the present invention, a manufacturing apparatus 50 can be used as shown in FIG. 7, for example.

The manufacturing apparatus 50 includes a first metallic powder containing material supply unit 61, a second metallic powder containing material supply unit 62, an extruder 60 having a pressing mechanism (for example, an oil hydraulic cylinder) 63, a binder removing furnace 65, a sintering furnace 66, and a winder 67. Furthermore, the manufacturing apparatus 50 includes a control unit 68 for controlling the first metallic powder containing material supply unit 61, the second metallic powder containing material supply unit 62, and the pressing mechanism 63.

First, a first metallic powder containing material and a second metallic powder containing material are prepared. As a first metallic powder and a second metallic powder, those described above are used. The average grain diameters of the metallic powders are preferably about 10 to 30 µm. Then, the first metallic powder is kneaded with a binder to prepare the first metallic powder containing material. Similarly, the second metallic powder is kneaded with a binder to prepare the second metallic powder containing material. As the binders, a variety of organic binders can be used, for example, paraffin wax is preferable. Furthermore, molding assistants may be added to the metallic powder containing materials. Examples of the molding assistant include lubricants and polyethylene. Besides, the first and second metallic powder containing materials are preferably palletized. This facilitates the feeding of the metallic powder containing materials into the respective supply units.

Then, the first metallic powder containing material prepared as above is fed into the supply portion 61, whereas the second metallic powder containing material prepared as above is fed into the supply unit 62, and the manufacturing apparatus 50 is operated to extrude the molding material while continuously supplying the kneaded forming material.

The kneaded forming material extruding step includes the distal end side portion forming material extruding stage for extruding the first metallic powder containing material into a filamentous shape, the proximal end side portion forming material extruding stage for extruding the second metallic powder containing material into a filamentous shape, and the intermediate portion forming material extruding stage which is provided between, and continuous with, the distal end side portion forming material extruding stage and the proximal end side portion forming material extruding stage and which is for extruding the material containing the first metallic powder and the second metallic powder. Furthermore, in the intermediate portion forming material extruding stage, the extrusion is so conducted that the content of the first metallic powder in the intermediate portion forming material decreases while the content of the second metallic powder in the intermediate portion forming material increases as the proximal end side portion forming material extruding stage is approached.

Specifically, the control unit 68 has the function of controlling the first metallic powder containing material supply unit 61 and the second metallic powder containing material supply unit 62. For example, immediately after the operation of the manufacturing apparatus is started, the control unit 68 performs such a control that the extruder 60 is supplied with the material only from the first metallic powder containing material supply unit 61. This ensures that the extrudate 70 discharged from the extruder 60 contains the first metallic powder material but does not contain the second metallic powder material. Thus, the distal end side portion forming material extruding stage for extruding the first metallic powder containing material into a filamentous shape is carried out. In the distal end side portion forming material extruding stage, the diameter of the extrudate 70 may be locally varied by regulating the quantity of the material discharged per unit time or by regulating the die or nozzle in the extruder. The variation pattern of the diameter of the extrudate 70 is preferably the one described with respect to the guide wire shown in FIG. 1 above.

Subsequently, after a predetermined length of the extrudate 70 is discharged, the control unit 68 controls the first metallic powder containing material supply unit 61 and the second metallic powder containing material supply unit 62 so as to decrease continuously (or gradually) or stepwise the quantity of the first metallic powder containing material supplied and to increase continuously (or gradually) or stepwise the quantity of the second metallic powder containing material supplied. The first metallic powder containing material and the second metallic powder containing material supplied into the extruder is kneaded with each other in the extruder, before being discharged therefrom. In this manner, the intermediate portion forming material extruding stage for extruding the material containing the first metallic powder and the second metallic powder is carried out. During the intermediate portion forming material extruding stage, the content of the first metallic powder in the intermediate portion forming material decreases, whereas the content of the second metallic powder in the intermediate portion forming material increases. To be more specific, when the intermediate portion forming material extruding stage is started, the supplied quantity of the first metallic powder containing material decreases whereas the supplied quantity of the second metallic powder containing material increases, with time. When a forming time has passed, the supplied quantity of the first metallic powder containing material reaches 0 (zero), and the intermediate portion forming material extruding stage ends. The quantity of the material discharged per unit time during the intermediate portion forming material extruding stage is preferably equal to the quantity of the material discharged per unit time at the end of the distal end side portion forming material extruding stage.

Then, after a predetermined length of the kneaded material 70 is extruded, the control unit 68 controls the first metallic powder containing material supply unit 61 and the second metallic powder containing material supply unit 62 so as to stop the supply of the first metallic powder containing material and to supply only the second metallic powder containing material. After a predetermined length of the extrudate 70 formed from the second metallic powder containing material is discharged, the control unit 68 stops the supply of the second metallic powder containing material. In this way, the proximal end side portion forming material extruding stage for extruding the second metallic powder containing material is carried out.

Subsequently, the binder removing step is conducted. Specifically, the extrudate 70 discharged from the extruder enters the binder removing furnace 65, and is deprived of the binder while passing through the binder removing furnace 65. The binder removing step is a heating step. The binder removing step is conducted under the condition where there is a certain difference between the temperature upon the entrance of the extrudate 70 into the binder removing furnace 65 and the maximum heating temperature inside the furnace 65. Namely, the temperature at the entrance of the furnace 65 is lower, and the temperature becomes higher as the extrudate 70 proceeds through the furnace 65. The temperature may be constant over the range from an intermediate portion to the exit of the furnace 65. The temperature difference inside the furnace 65 is preferably about 100 to 600° C. With the initial temperature thus set to be lower, it is possible to prevent abrupt removal of the binder. Besides, the binder removal time (the period of time from the entrance of the extrudate 70 into the furnace 65 to the discharge of the extrudate 70 from the furnace 65) is preferably 10 to 20 min, particularly 10 to 15 min.

Subsequently, the sintering step is conducted. Specifically, the extrudate 70 discharged from the binder removing furnace 65 enters the sintering furnace 66, and is sintered while passing through the sintering furnace 66. The so-called sintering temperature is preferably 1000 to 1600° C. Besides, the sintering time (the period of time from the entrance of the extrudate 70 into the sintering furnace 66 to the discharge of the extrudate 70 from the furnace 66) is preferably 10 to 20 min, particularly 10 to 15 min.

Next, the winding step is conducted. Specifically, the sintered body (wire) discharged from the sintering furnace 66 is wound on the winder 67. As the winder 67, a drum is used. In this manner, a guide wire is manufactured. The winding step may not necessarily be performed.

According to this manufacturing method, the guide wire is manufactured as an integral body which includes the distal end side portion 2, the intermediate portion 4 having a gradient physical property portion, and the proximal end side portion 3 and which does not include any joint portion.

In this embodiment, the kneaded forming material extruding step is performed by first carrying out the distal end side portion forming material extruding stage, then carrying out the intermediate portion forming material extruding stage, and finally carrying out the proximal end side portion forming material extruding stage. This, however, is not limitative. The kneaded forming material extruding step may be performed by first carrying out the proximal end side portion forming material extruding stage, then carrying out the intermediate portion forming material extruding stage, and finally carrying out the distal end side portion forming material extruding stage. In this case, the intermediate portion forming material extruding stage is so conducted that the content of the first metallic powder in the intermediate portion forming material increases whereas the content of the second metallic powder in the intermediate portion forming material decreases, as the distal end side portion forming material extruding stage is approached.

The guide wire manufactured as described above is preferably subjected to a resin coating step for coating the outer surface of the guide wire with a resin. As the resin, those mentioned above can be used. The coating can be carried out by a known method such as immersion in a solution of the resin, a method of passing the guide wire through a heated die while supplying the resin thereto, etc.

EXAMPLE 1

A wire material made of a stainless steel (SUS304L) and having a length of 500 mm and a diameter of 0.35 mm was prepared. In addition, a wire material made of a Ni—Ti alloy and having a length of 500 mm and a diameter of 0.35 mm was prepared, and an end portion of the Ni—Ti alloy wire material was processed into the shape of a distal end portion of a guide wire.

Next, a stainless steel powder (a SUS304L powder, produced by Kojundo Chemical Laboratory Co., Ltd.; product code: FEA01PB; average grain diameter: 75 μm) and a Ni—Ti alloy powder (a product by Kojundo Chemical Laboratory Co., Ltd.; product code: NIA11PB; average grain diameter: 75 μm) were prepared. The powders were weighed in SUS304L:Ni—Ti alloy weight ratios of 90:10, 80:20, 70:30, 60:40, 50:50, 40:60, 30:70, 20:80, and 10:90, followed by mixing, to prepare nine kinds of mixtures.

Then, a cylindrical member made of SUS304L and having a diameter of 20 mm and a thickness of 30 mm was placed in a sintering chamber of a sintering apparatus (SPS-511S, a discharge plasma sintering apparatus produced by Sumitomo Coal Mining Co., Ltd.), and the nine kinds of mixtures prepared above were sequentially layered on the cylindrical member in the order of decreasing SUS304L content so that each mixture layer had a diameter of 20 mm and a thickness of 5 mm (the total thickness: 45 mm). Thereafter, a cylindrical member made of a nickel-titanium alloy and having a diameter of 20 mm and a thickness of 30 mm was placed on the laminate of the mixtures.

Next, by use of the discharge plasma sintering apparatus, sintering was carried out at a pressure of about 40 MPa and a sintering temperature of about 1300° C. for about 15 min, to obtain a sintered body. Then, by use of discharge wire cutting, the sintered body was cut to an elongate cylindrical shape having a length of 50 mm and a diameter of 0.5 mm, followed by polishing by use of a cylindrical grinder, to obtain a gradient physical property portion wire material having a length of 30 mm and a diameter of 0.35 mm.

Then, the proximal end of the Ni—Ti alloy wire material was joined to the higher Ni—Ti alloy content side of the intermediate portion forming wire material, and the higher SUS304L content side of the gradient physical property portion wire material was joined to the SUS304L wire material, by use of a resistance welding machine, to obtain a guide wire according to the present invention.

EXAMPLE 2

A wire material made of a stainless steel (SUS304L) and having a length of 500 mm and a diameter of 0.35 mm was prepared. In addition, a wire material made of a Ni—Ti alloy and having a length of 500 mm and a diameter of 0.35 mm was prepared, and an end portion of the Ni—Ti alloy wire material was processed into the shape of a distal end portion of a guide wire.

Next, a stainless steel powder (a SUS304L powder produced by Kojundo Chemical Laboratory Co., Ltd.; product code: FEA01PB; average grain diameter: 75 μm) and a Ni—Ti alloy powder (a product by Kojundo Chemical Laboratory Co., Ltd.; product code: NIA11PB; average grain diameter: 75 μm) were prepared. By use of respective exclusive-use powder metering apparatuses (KCL24KQX2, loss-in-weight type feeders produced by K-Toron), the two powders were supplied in such a manner that the initial supply quantity of the SUS304L powder was 2 g/min, the initial supply quantity of the Ni—Ti alloy powder was 0.2 g/min, the supply quantity of the SUS304L powder was continuously decreased at a rate of 0.2 g/min, and the supply quantity of the Ni—Ti alloy powder was continuously increased at a rate of 0.2 g/min. The supply of the powders was continued until the thickness of the mixture layer, in which the content of the second metallic material varied continuously, reached 20 mm.

Next, the powders supplied from the powder metering apparatuses were fed into a powder stirrer-mixer, in which the powders were mixed uniformly, and the resulting powder mixture was fed into and stacked in a sintering chamber, to obtain a powder stack in which the composition of the mixture of the two kinds of powders varied continuously. A cylindrical member made of SUS304L and a cylindrical member made of the Ni—Ti alloy were placed respectively on both ends of the powder stack, in the same manner as in Example 1.

Subsequently, by use of a discharge plasma sintering apparatus, sintering was conducted at a pressure of about 40 MPa and a sintering temperature of about 1300° C. for about 15 min, to obtain a sintered body. Then, by use of discharge wire cutting, the sintered body was cut to an elongate cylindrical shape having a length of 50 mm and a diameter of 0.5 mm, followed by polishing by use of a cylindrical grinder, to obtain a gradient physical property portion wire material having a length of 30 mm and a diameter of 0.35 mm.

Then, the proximal end of the Ni—Ti alloy wire material was joined to the higher Ni—Ti alloy content side of the intermediate portion forming wire material, and the higher SUS304L content side of the gradient physical property portion wire material was joined to the SUS304L wire material, by use of a resistance welding apparatus, to obtain a guide wire according to the present invention.

The guide wire according to the present invention is characterized in that the proximal end side portion has a sufficient rigidity, while the distal end side portion has a certain degree of flexibility, and the guide wire as a whole is high in torque transmission performance and pushability.

Where the content of the second metallic material in the gradient physical property portion is set to increase stepwise from the distal end side toward the proximal end side, the physical properties of the gradient physical property portion do not vary abruptly but vary gradually, so that the guide wire shows favorable operationality.

Where the content of the second metallic material in the gradient physical property portion is set to increase continuously from the distal end side toward the proximal end side, the physical properties of the gradient physical property portion do not vary abruptly but vary more gradually, so that the guide wire shows favorable operationality.

Where the first metallic material is a Ni—Ti based alloy, the distal end side portion of the guide wire has sufficient elasticity and flexibility, and the intermediate portion of the guide wire has favorable gradient physical properties.

Where the second metallic material is a stainless steel, the proximal end side portion of the guide wire has a sufficient rigidity, promising a favorable operationality.

Where the guide wire comprises a coil portion provided so as to cover a distal end portion of the guide wire, insertion of the guide wire to a target site is further facilitated.

Where the coil portion is formed of a high-contrast material, it is easy to confirm the position of the distal end portion of the guide wire by radiography or echography.

Where one end portion of the gradient physical property portion is formed only of the first metallic material and the other end portion is formed only of the second metallic material, continuity of physical properties between the distal end side portion and the gradient physical property portion and between the gradient physical property portion and the proximal end side portion is secured, and, where the portions are connected by joining, the joining is easy to achieve.

Where the guide wire is an integral body which does not have any joint portion, the guide wire as a whole does not have any point of abrupt change in physical properties, so that the guide wire has a favorable operationality.

In addition, a method of manufacturing a guide wire according to the present invention includes the steps of: preparing a distal end side portion forming wire material made of the first metallic material and a proximal end side portion forming wire material made of the second metallic material; charging a mold with a powder of the first metallic material and a powder of the second metallic material so that the content of the first metallic material powder increases whereas the content of the second metallic material powder decreases, from one side toward the other side; sintering the metallic powder charge to produce an intermediate portion forming member having a gradient physical property portion; and joining the proximal end side portion forming wire material to one side of the intermediate portion forming member and joining the distal end side portion forming wire material to the other side of the intermediate portion forming member.

Therefore, it is possible to manufacture easily and securely a guide wire which has the above-mentioned gradient physical property portion.

Where the metallic powder charging step consists in charging the mold with the first metallic material powder and the second metallic material powder to form a plurality of layers in which the content of the first metallic material in the charge increases stepwise and the content of the second metallic material in the charge decreases stepwise, it is possible to easily manufacture a guide wire having a gradient physical property portion of which physical properties vary gradually.

Where the metallic powder charging step consists in charging the mold with the first metallic material powder and the second metallic material powder so that the content of the first metallic material in the charge increases continuously and the content of the second metallic material in the charge decreases continuously, it is possible to easily manufacture a guide wire having a gradient physical property portion of which physical properties vary more gradually.

Besides, a method of manufacturing a guide wire according to the present invention comprises a step of continuously extruding into a filamentous shape a kneaded forming material containing a metallic powder for forming the guide wire, and a step of sintering the filamentous body thus extruded. The kneaded forming material extruding step comprises: a distal end side portion forming material extruding stage for extruding a material containing the first metallic powder into a filamentous shape; a proximal end side portion forming material extruding stage for extruding a material containing the second metallic material into a filamentous shape; and an intermediate portion forming material extruding stage which is provided between, and continuous with, the distal end side portion forming material extruding stage and the proximal end side portion forming material extruding stage and which is for extruding a material containing the first metallic powder and the second metallic powder. In the intermediate portion forming material extruding stage, the extrusion is so conducted that the content of the first metallic powder in the intermediate portion forming material decreases and the content of the second metallic powder in the intermediate portion forming material increases as the proximal end side portion forming material extruding stage is approached. Therefore, it is possible to manufacture easily and securely a guide wire having the above-mentioned gradient physical property portion.

The present invention is not limited to the details of the above described preferred embodiments. The scope of the invention is defined by the appended claims and all changes and modifications as fall within the equivalence of the scope of the claims are therefore to be embraced by the invention.

The invention claimed is:

1. A guide wire comprising:
   a distal end side portion having a proximal end and formed of a first metallic material,
   a proximal end side portion having a distal end and formed of a second metallic material higher in rigidity than said first metallic material, and
   an intermediate portion provided between said distal end side portion and said proximal end side portion, having a proximal end and a distal end, said intermediate portion being formed of a metallic material mixture of said first metallic material and said second metallic material, wherein said intermediate portion comprises an integral gradient composition portion having a predetermined length in which a weight ratio of said first metallic material in the metallic material mixture decreases and a weight ratio of said second metallic material in the metallic material mixture increases along the length of said intermediate portion, from the distal end side portion toward the proximal end side portion, wherein said distal end of said intermediate portion is joined to a terminal end of said proximal end of said distal end side portion and said proximal end of said intermediate portion is joined to a terminal end of said distal end of said proximal end side portion such that said distal end side portion and said proximal end side portion do not overlap, said intermediate portion comprising a sintered cylindrical body formed of a powder of said first metallic material and a powder of said second metallic material.

2. The guide wire as set forth in claim 1, wherein the weight ratio of said second metallic material in the metallic material mixture in said gradient physical property portion increases stepwise from the distal end side toward the proximal end side.

3. The guide wire as set forth in claim 1, wherein the weight ratio of said second metallic material in the metallic material mixture in said gradient physical property portion increases continuously from the distal end side toward the proximal end side.

4. The guide wire as set forth in claim 1, wherein said first metallic material is a Ni—Ti based alloy.

5. The guide wire as set forth in claim 1, wherein said second metallic material is a stainless steel.

6. The guide wire as set forth in claim 1, which comprises a coil portion so provided as to cover a distal end portion thereof.

7. The guide wire as set forth in claim 6, wherein said coil is formed of a contrast material.

8. The guide wire as set forth in claim 1, wherein at least a portion of an outer surface of said guide wire is coated with a resin.

9. The guide wire as set forth in claim 1, wherein a distal end portion of said intermediate portion is formed only of said first metallic material, and a proximal end portion of said intermediate portion is formed only of said second metallic material.

10. The guide wire as set forth in claim 1, wherein said intermediate portion is joined to said distal end side portion and said proximal end side portion by welding.

11. The guide wire as set forth in claim 1, which is an integral body free of any joint portion.

12. The guide wire as set forth in claim 1, wherein said intermediate portion is a cylindrical filamentous portion.

13. A guide wire comprising a distal end side portion having a proximal end and formed of a first metallic material, a proximal end side portion having a distal end and formed of a second metallic material higher in rigidity than said first metallic material, and an intermediate portion provided between said distal end side portion and said proximal end side portion and having a proximal end and a distal end, wherein said intermediate portion comprises a sintered cylindrical body formed of a powder of the first metallic material and a powder of the second metallic material, wherein said intermediate portion comprises a gradient composition portion having a predetermined length in which a weight ratio of said first metallic material in the metallic material mixture decreases from the distal end side portion toward the proximal end side portion, a distal end of said intermediate portion is formed of said first metallic material, and said distal end of said intermediate portion is joined to said distal end side portion by welding, and wherein said distal end of said intermediate portion is joined to said proximal end of said distal end side portion and said proximal end of said intermediate portion is joined to said distal end of said proximal end side portion.

14. The guide wire as set forth in claim 13, wherein said intermediate portion is a cylindrical filamentous portion.

15. A guide wire comprising a distal end side portion having a proximal end and formed of a first metallic material, a proximal end side portion having a distal end and formed of a second metallic material higher in rigidity than said first metallic material, and an intermediate portion provided between said distal end side portion and said proximal end side portion, having a proximal end, a distal end, and an integral portion having a predetermined length which is formed of a metallic material mixture containing said first metallic material and said second metallic material, wherein in said integral portion of said intermediate portion a weight ratio of said first metallic material in the metallic material mixture decreases from the distal end side portion toward the proximal end side portion and a weight ratio of said second metallic material increases from the distal end side portion toward the proximal end side portion so as to define a nonuniform composition along the length of said integral portion, wherein a distal end of said intermediate portion is formed of said first metallic material, and a proximal end of said intermediate portion is formed of said second metallic material, wherein said distal end of said intermediate portion is joined to said proximal end of said distal end side portion by welding and said proximal end of said intermediate portion is joined to said distal end of said proximal end side portion by one of welding, soldering or brazing such that said proximal end of said distal end side portion and said distal end of said proximal end side portion do not overlap, and wherein said intermediate portion comprises a sintered cylindrical body formed of a powder of said first metallic material and a powder of said second metallic material.

16. The guide wire as set forth in claim 15, wherein said intermediate portion is a cylindrical filamentous portion.

17. A guide wire comprising a distal end side portion having a proximal end and formed of a first metallic material, a proximal end side portion having a distal end and formed of a second metallic material higher in rigidity than said first metallic material, and an integral intermediate portion provided between said distal end side portion and said proximal end side portion and having a proximal end and a distal end and formed of a metallic material mixture containing said first metallic material and said second metallic material, said intermediate portion comprises a gradient composition portion having a predetermined length in which a weight ratio of said first metallic material decreases from the distal end side toward the proximal end side, and in which a weight ratio of said second metallic material in the metallic material mixture increases along the length of said intermediate portion from the distal end side toward the proximal end side, wherein a distal end of said intermediate portion is formed only of said first metallic material, and a proximal end of said intermediate portion is formed only of said second metallic material, wherein said distal end of said intermediate portion is joined to said distal end side portion by welding and said proximal end of said intermediate portion is joined to said proximal end side portion by one of welding, soldering or brazing such that said proximal end of said distal end side portion and said distal end of said proximal end side portion do not overlap, and wherein said intermediate portion comprises a sintered cylindrical body formed of a powder of said first metallic material and a powder of said second metallic material.

18. The guide wire as set forth in claim 17, wherein said intermediate portion is a cylindrical filamentous portion.

19. A guide wire comprising:

a distal end side portion having a proximal end and formed of a first metallic material, a proximal end side portion having a distal end and formed of a second metallic material higher in rigidity than said first metallic material, and an intermediate portion provided between said distal end side portion and said proximal end side portion, wherein said intermediate portion comprises a sintered cylindrical body formed of a first metallic member made of said first metallic material, a second metallic member made of said second metallic material, and a metallic material mixture of a powder of said first metallic material and a powder of said second metallic material charged between said first metallic member and said second metallic member, wherein in said metallic material mixture a mixing ration of said first metallic material decreases and a mixing ration of said second metallic material increases from the distal end side toward the proximal end side, and wherein said first metallic member of said intermediate portion is joined to said proximal end of said distal end side portion and said second metallic member of said intermediate portion is joined to said distal end of said proximal end side portion.

* * * * *